United States Patent [19]
Suzanne et al.

[11] Patent Number: 5,212,991
[45] Date of Patent: May 25, 1993

[54] PORTABLE, SELF-CONTAINED EQUIPMENT FOR THE IN SITU ANALYSIS OF A LIQUID OR SOLID SUBSTANCE

[75] Inventors: Pierre Suzanne, Oncy sur Ecole; Patrick Bleuse, Le Quesnoy; Gilles Guene, Elancourt; Christian Heurtel, Vert le Petit, all of France

[73] Assignees: Proengin S.A.; Etat Francais, both of France

[21] Appl. No.: 651,331

[22] PCT Filed: Jun. 7, 1990

[86] PCT No.: PCT/FR90/00399
§ 371 Date: Feb. 7, 1991
§ 102(e) Date: Feb. 7, 1991

[87] PCT Pub. No.: WO90/15318
PCT Pub. Date: Dec. 13, 1990

[30] Foreign Application Priority Data
Jun. 9, 1989 [FR] France .................. 89 07985

[51] Int. Cl.⁵ ............................. G01N 1/02
[52] U.S. Cl. .................. 73/863.11; 73/864.34; 73/864.71; 73/23.2
[58] Field of Search ........... 73/863.11, 863.12, 864.71, 73/864.34, 23.2, 31.03

[56] References Cited
U.S. PATENT DOCUMENTS

| | | | |
|---|---|---|---|
| 4,348,887 | 9/1982 | Lorenz et al. | 73/23.2 |
| 4,458,541 | 7/1984 | Deming et al. | 73/863.11 |
| 4,541,268 | 9/1985 | Odenheimer | 73/31.07 |
| 4,542,641 | 9/1985 | Eyler | 73/863.12 X |
| 4,599,095 | 7/1986 | Barnes et al. | 55/269 X |
| 4,848,167 | 7/1989 | Gordon et al. | 73/864.71 |
| 4,909,090 | 3/1990 | McGowan | 73/863.12 |
| 4,974,455 | 12/1990 | McGowan | 73/863.12 |
| 5,162,233 | 11/1992 | Komuri et al. | 73/863.11 X |

FOREIGN PATENT DOCUMENTS 2595470 9/1987 France.
2088055 6/1982 United Kingdom.

Primary Examiner—Tom Noland
Attorney, Agent, or Firm—William A. Drucker

[57] ABSTRACT

The invention relates to equipment which includes a device for the analysis of gaseous compositions (1) to which is attached a device (16) for taking a sample of the substance to be analyzed and then vaporizing it. The analysis device (1) is connected to the sampling device (16) in such a way that it can use the vapors produced by the latter as a gaseous composition. The substance to be analyzed may consist of a liquid, or even of solid particles. The invention makes it possible to detect contaminated zones as well as the composition of the substances which cause contamination.

12 Claims, 4 Drawing Sheets

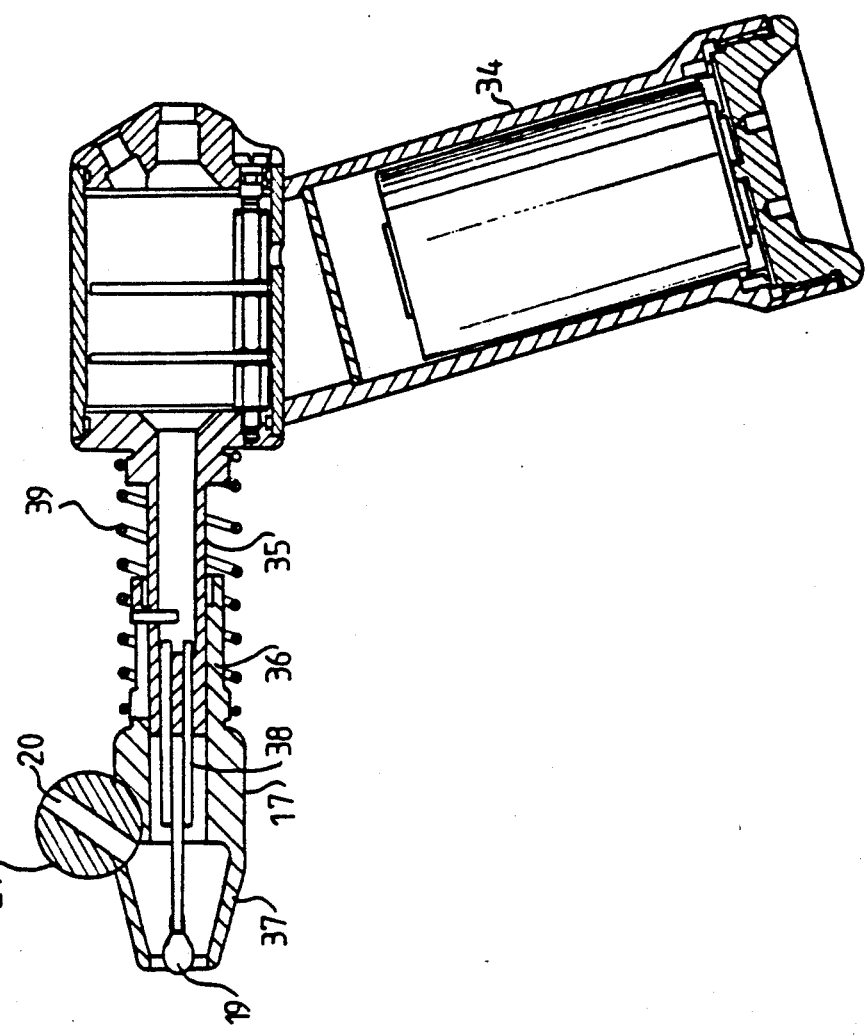

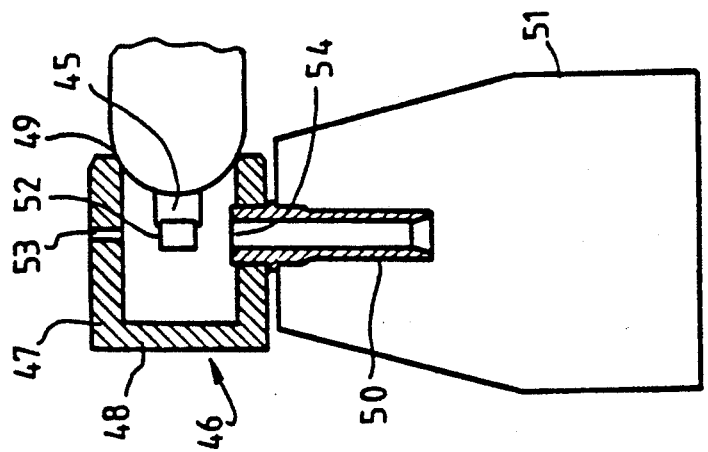
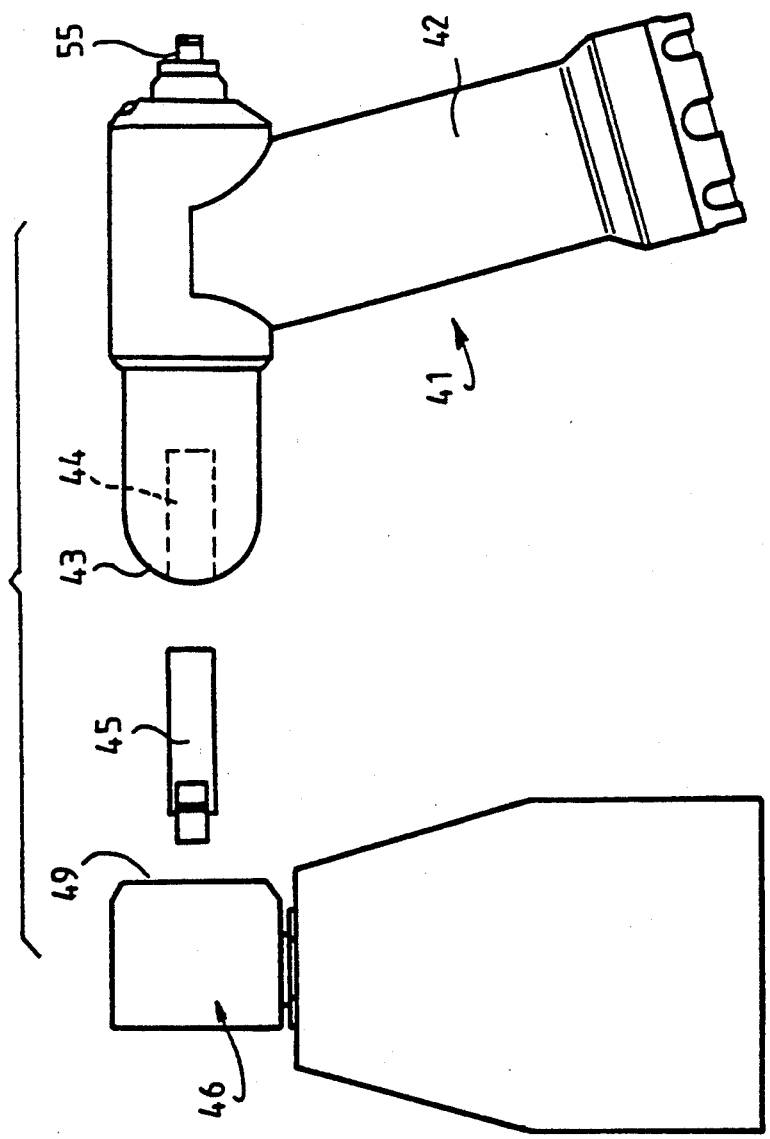

5,212,991

PORTABLE, SELF-CONTAINED EQUIPMENT FOR THE IN SITU ANALYSIS OF A LIQUID OR SOLID SUBSTANCE

BACKGROUND OF THE INVENTION

The invention relates to a portable and self-contained apparatus for analyzing in situ a liquid or solid substance which may in particular be in the form of surface deposits.

Generally, in the panoply of chemical weapons are included substances of very high toxicity, intended to be spread (for example from a bomb) in the form of fine droplets or fine particles spaced relatively to each other, simple contact of one of these droplets or these particles with the skin or a mucous membrane of an individual being possibly dangerous for this individual. The same goes for certain contaminants of industrial origin.

It is then important to be able to detect the existence of contaminated zones and rapidly determine the composition of the toxic substance, as well as the density with which the droplets or particles have been spread.

Now, at the present time, no self-contained portable apparatus exists, of small size, which makes it possible to obtain instantaneously all this information on the site, the solution envisaged consisting in taking samples and then sending them to a laboratory for analysis.

On the other hand, portable apparatus are at present produced for analyzing a gaseous composition for detecting the presence of and analyzing polluting or dangerous gases.

The invention proposes then filling the gap mentioned above by associating a portable gas composition analysis apparatus and a device for taking the sample and vaporizing the substance to be analyzed, it being understood that in this case the vapours produced by the sample taking device are used by the analysis apparatus as gas composition to be analyzed.

The problem which then arises concerns the design of a sample taking device for taking a sample of the substance to be analyzed then evaporating it so that the vapour released may be totally sucked in by the analysis apparatus.

To this problem is added the one due to the fact that these different operations must be carried out while avoiding any possibility of contamination which would lead to falsifying the analysis made subsequently.

SUMMARY OF THE INVENTION

To solve these problems, the invention proposes a portable and self-contained apparatus for analyzing a substance in situ, this apparatus comprising a gas composition analysis device with which is associated a device for taking the sample on a support then vaporizing the substance taken by heating said support using heating means incorporated in said support, the analysis device being connected to the sample taking device so as to use the vapours produced by said heating as gas composition to be analyzed.

According to the invention, this apparatus is characterized in that it comprises a collecting enclosure whose internal volume is connected to suction means of the analysis device and in which said support is engaged during the vaporization phase, the support being outside this enclosure during the sample taking phase.

In the case where the substance to be analyzed is liquid or gaseous, the sample taking head may comprise a flexible tongue covered with an absorbent layer, said heating means then consisting of an electric heating resistance carried by the tongue. This electric heating resistance may be supplied with power from an electric energy source housed in said body and controlled by a switch actuated as a function of the relative position of the sample taking head and the enclosure.

Advantageously, said layer may be designed so as to selectively absorb and so concentrate the products which it is desired to reveal. It may, in particular, comprise a silica gel deposited on the surface and held in position by silicon.

Furthermore, in order to determine the total amount of a constituent of the liquid sample taken, the device of the invention may comprise integration means adapted for integrating in time the instantaneous values delivered by the analysis apparatus, these integration means being initialized at the time of actuation of said switch controlling the use of the heating means.

BRIEF DESCRIPTION OF THE DRAWING

One embodiment of the invention will be described hereafter, by of non limitative example, with reference to the accompanying drawings in which:

FIG. 4 is an axial section of the sample taking and vaporization device shown in FIGS. 2 and 3;

FIG. 5 is a partial schematic section of a removable sample taking head which can be used in the apparatus shown in FIGS. 2 to 4;

FIG. 6 is a partial section of a flexible tongue which can be used in the sample taking head shown in FIG. 5;

FIG. 7 is a side view of a variant of construction of the sample taking and vaporization device according to the invention, in the disassembled position; and FIG. 8 is a partial axial section showing the device of FIG. 7 in the assembled position.

DETAILED DESCRIPTION

Figure 1:
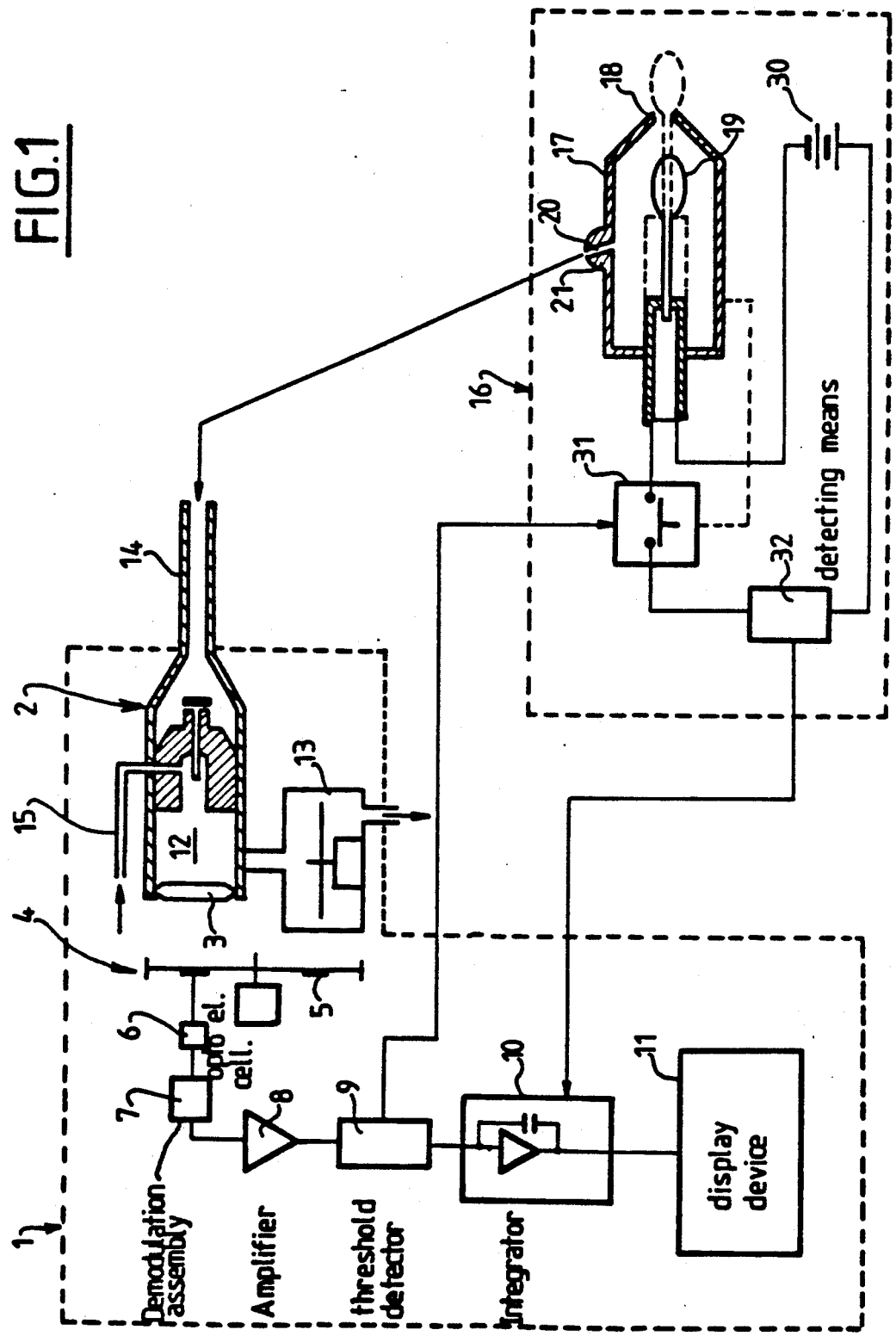
FIG. 1 is a schematic representation illustrating the principle of an apparatus according to the invention intended more particularly for analyzing toxic liquids.

In the example shown in FIG. 1, the apparatus for analyzing toxic liquids uses a portable and self-contained detector 1 providing in real time the analysis of a gas composition by flame spectrography, for example in the way described in the patent FR 87 02762 of Mar. 2, 1987, to PROENGIN.

This apparatus 1 comprises more particularly a burner with a window equipped with a focalizing optical system 3 in the axis of which are disposed successively a rotary chopper 4 comprising a plurality of optical filters 5, at the rate of one per characteristic spectral line of the element sought, and an opto-electronic cell 6 placed in the focussing zone of the optical system 3.

The electric signal delivered by cell 6 is transmitted to an electronic processing circuit comprising successively a demodulation assembly 7, an amplifier 8, a threshold detector 9, an integrator 10 and a display device 11.

Burner 2 comprises a combustion chamber 12 kept under depression by means of a turbine 13. It is connected to the outside through a suction nozzle 14, and to a circuit 15 for the admission of a hydrogen flow at a constant rate.

The sample taking and vaporization device associated with this analysis apparatus has been shown schematically in FIG. 1 inside block 16. It comprises, as mentioned above, a collecting enclosure 17 open on one side through an opening 18 and a sample taking head 19 which is movable relatively to this enclosure 17 so as to be able to occupy successively a vaporization position (continuous lines) in which it is housed inside enclosure 17, and a sample taking position (broken lines) in which it extends at least partially outside the enclosure 17 after passing through opening 18. Enclosure 17 further comprises an orifice 20 with a coupling head 21 intended to be connected to the suction nozzle 14 of the analysis apparatus 1.

The sample taking head 19 may consist, as shown in FIGS. 4 and 5, of a tongue 22 forming a loop and both ends 23, 24 of which are fixed respectively to the two faces of a rigid support rod 25.

This tongue 22 has a multi-layer structure comprising two layers 26, 27 made from an electrically insulating plastic material and between which is disposed an electric heating resistance 28 and, disposed on the external face of layer 24, an outer absorbent layer 29.

The electric energy supply for the heating resistance 28 is provided by an electric current supply source 30 such, for example, as a battery of cells or accumulators. This source is connected to the electric heating resistance 28 via an electric circuit comprising a switch 31 whose closure is controlled automatically by a mechanical connection, when head 19 is in the vaporization position and the opening of which is controlled by the threshold detector 9 and/or by position detection means, when head 19 is in the sample taking position.

This circuit further comprises means 32 for detecting closure of switch 31 and initializing the integration circuit 10 of the analysis apparatus 1.

Figure 2:
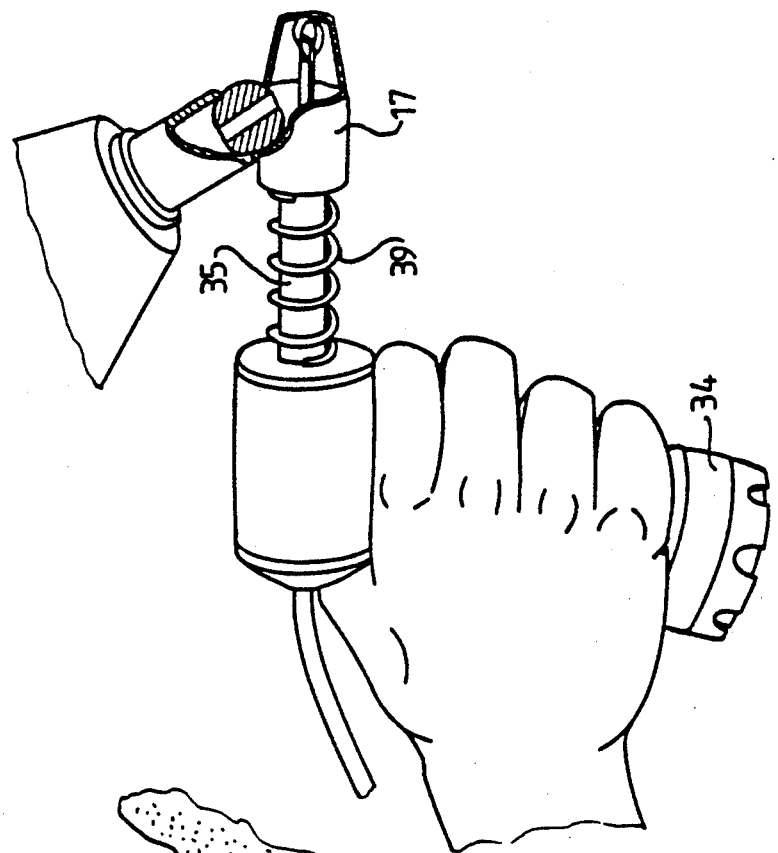
FIGS. 2 and 3 are two schematic perspective views showing one method of using a sample taking and vaporization device.
Figure 3:
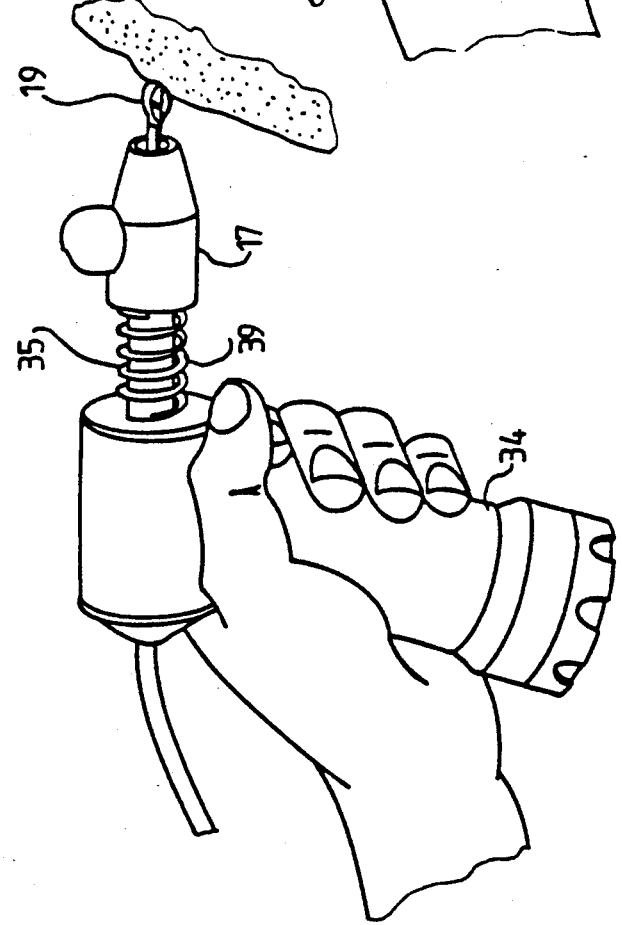

From the structural point of view, the sample taking and vaporization device may comprise, as shown in FIGS. 2, 3 and 6, a body in the form of a gun whose handle 36 serves as container for the electric energy source 30 and whose portion corresponding to the barrel consists of a tubular element 35 at the end of which the collecting enclosure 17 is mounted axially for sliding. This enclosure 17 has a cylindrical-truncated cone shape whose cylindrical portion 36 slides on the tubular element 35 and whose truncated cone shaped portion 37 open at the level of the truncated face serves for receiving the sample taking head 19.

In this example, the sample taking head 19 is of the type which can be thrown away after use and is mounted on the end of a tubular element 35 by means of a resilient clip 38 which further provides the electric connection thereof with the supply circuit.

In the rest state, the collecting enclosure 17 is in the retracted position (head 19 being in the sample taking position). It may be brought to the extended position (which corresponds to the vaporization position of the head) against the action of a traction spring 39.

Enclosure 17 is coupled to the suction nozzle 14 of the analysis apparatus by means of a substantially spherical coupling head 21 pierced with a channel 20 communicating with the inner volume of enclosure 17.

Operation of the above described apparatus is the following.

To take a sample, the operator holds the handle of the sample taking device as shown in FIG. 2, enclosure 17 at rest being retracted and letting the sample taking head 19 pass.

A drop is then taken by bringing the sample taking head 19 in contact with the drop, so that the toxic liquid is absorbed by the absorbent layer.

The operator then couples the suction nozzle of the analysis apparatus by pushing enclosure 17 axially so as to place it in the extended position.

In this position, the enclosure acts on the switch so as to close the supply circuit for the heating resistance. At the same time, the detector transmits an initialization signal to the integrator.

The heating resistance causes evaporation of the liquid absorbed by the layer. The mixture of air and vapour contained in enclosure 17 is sucked in by the action of turbine 13 and passes successively through nozzle 14 and into the combustion chamber 12 of the burner. The flame obtained by combustion of the gaseous mixture in the hydrogen stream generates light radiation which, for each frequency spectrum corresponding to the elements sought, gives rise at the output of detector 6 to a signal of variable intensity whose integration makes it possible to determine the total amount of elements sought which are present in head 19.

The threshold detector is designed so as to emit a signal indicating absence of the element sought, either because the sampled liquid does not contain any or because the sampled liquid has completely evaporated. In this case, the threshold detector serves for opening the switch and stopping the integration taking place.

Of course, the invention is not limited to the embodiment described above.

Thus, in particular, the sample taking head could comprise a multiplicity of tongues disposed side by side over a relatively great length, so as to be able to sweep a zone of known area. In this case, the result delivered by the integrator may be used for determining the amount of toxic liquid per unit of area.

The collecting enclosure associated with such a sample taking head may then be made in two parts hinged together so as to be able to open and allow samples to be taken and closed for collecting the vapors of the liquid sampled by the head.

Furthermore, in the case where the substance to be analyzed is in the form of solid particles, the absorbent layer coating the sample taking head may be replaced by an adhesive layer on which the particles may be fixed. In this case, operation of the sample taking device remains the same as that described above.

In the example shown in FIGS. 7 and 8, the sample taking and vaporization device is made in two separate parts, namely:

a sample taking instrument 41 in the form of a gun whose handle 42 serves as container for an electric energy source and whose portion corresponding to the barrel ends in a hemispherical end-piece 43, with an axial receptacle 44 in which a removable sample taking head 45, of the type described above, may be engaged and connected electrically, and a vapour collector 46 substantially in the form of a pipe comprising a tubular body 47 which defines a substantially cylindrical volume closed, on one side, by a bottom 48 and open, on the other side, through a circular opening 49 and a tubular connecting sleeve 50 whose internal volume communicates with the inner volume of body 47 and which projects radially with respect to the latter.

The connecting sleeve 50 is designed so as to be able to be connected to the suction nozzle of the analysis apparatus 51.

The tubular body 47 is designed so as to be applied on the hemispherical end-piece 43 of the sample taking instrument 41 so that the opening 49 is closed substantially sealingly and so that the loop 52 formed by the sample taking head is disposed coaxially to the connecting sleeve 50.

Furthermore, body 47 has an air intake orifice 53 situated at a position of the cylindrical wall of body 47, opposite the suction orifice 54 through which the connecting sleeve 50 emerges.

By means of the above described device, the sample is taken via the sample taking instrument 41 with its removable sample taking head 45.

Once the sample taken, instrument 41 is coupled to the vapour collector 46 (hemispherical end-piece 43 against the edge of opening 49) so that the sample taking head 45 is disposed as mentioned above.

Then, the product absorbed by the sample taking head 45 is vaporized by application of an electric current to the heating resistance incorporated in this head, for example by exerting a pressure on a push-button 55 for actuating a switch.

The vapour thus released is sucked in by the analysis apparatus 51 through the connecting sleeve 50. With the above described devices, during the suction phase, the sample taking head 45 is swept by a substantially coaxial air flow without forming any turbulence: thus the vapour produced does not contaminate the walls of the vapour collector 46.

Advantageously, the sample taking instrument will be equipped with a device for automatically ejecting the sample taking head, this device being designed so as to avoid any possible contamination of the operator by the used sample taking head.

We claim:

1. Portable and self-contained apparatus for analyzing a sample of a substance in situ, said apparatus comprising:
   i. a sample taking device comprising a body, a collecting enclosure having an external opening and a suction orifice, a sample taking head fixed to said body and at least partially lodged in said collecting enclosure, said sample taking head being provided with a support adapted to receive said sample, means for moving said sample taking head relatively to the collecting enclosure so as to occupy successively a sample taking position in which said support extends outside the collecting enclosure through said external opening so as to allow the sample to be taken, and a vaporization position in which said support is housed inside the collecting enclosure, and heating means designed so as to heat the support when the sample taking head is in the vaporization position and to vaporize said substance, and
   ii. a gas composition analysis device having a suction circuit connected to said suction orifice so as to use the vaporized substance as gas composition to be analyzed.

2. Apparatus according to claim 1, wherein said support comprises a flexible tongue coated with an absorbent layer adapted to absorb said substance.

3. Apparatus according to claim 2, wherein said layer comprises a silica gel deposited on said tongue and held by silicon.

4. Apparatus according to claim 2, wherein said heating means consist of an electric heating resistance carried by said support.

5. Apparatus according to claim 1, wherein said support comprises a flexible tongue coated with an adhesive layer.

6. Apparatus according to claim 1, wherein said support has a multi-layer structure with two layers made from an electrically insulating plastic material, between which is disposed an electric heating resistance and, disposed on the external surface of one of these two layers, an absorbent coating.

7. Apparatus according to claim 1, wherein the support comprises a flexible tongue disposed so as to form a loop, both ends of which are fixed respectively to said support.

8. Apparatus according to claim 7, wherein said support is intended to be removably mounted on an element fastened with the body of the sample taking device by mechanical connection means associated with electric connection means.

9. Apparatus according to claim 1, wherein the analysis device comprises means for producing an electric signal representative of an instantaneous amount of an element contained in the gas composition to be analyzed, and means for integrating said signal and means for initializing said integrating means when the sample taking head passes to the vaporization position, so that said integrating means determines the total amount of said element contained in the substance sampled by the sample taking head.

10. Apparatus according to claim 9, wherein the sample taking head comprises a multiplicity of tongues disposed side by side so as to be able to sweep a zone of known area, so that the integrating means used in the analysis device delivers information for deducing the amount of substance per unit area of the contaminated zone.

11. Apparatus according to claim 1, wherein said support has a multi-layer structure with two layers made from electrically insulating material, between which is disposed an electric heating resistance and, disposed on the external surface of one of these two layers, an adhesive coating.

12. Portable and self-contained apparatus for analyzing a sample of a substance in situ, said apparatus comprising:
   i. a sample taking device comprising a body having a sample taking head fixed to said body and provided with an extractable flexible tongue which serves to take said sample, said tongue being provided with an electric heating means for heating and vaporizing said sample;
   ii. a collecting enclosure having a suction orifice and an external opening through which said sample taking head may be engaged with said sample taken on said tongue; and
   iii. a gas composition analysis device having a suction circuit connected to said suction orifice so as to use the substance once heated and vaporized by said heating means as gas composition to be analyzed.

* * * * *